United States Patent
Binderup et al.

(10) Patent No.: US 7,253,193 B2
(45) Date of Patent: Aug. 7, 2007

(54) CYANOGUANIDINE PRODRUGS

(75) Inventors: Ernst Torndal Binderup, Taastrup (DK); Tore Duvold, Frederiksberg C (DK)

(73) Assignee: LEO Pharma A/S, Ballerup (DK)

( * ) Notice: Subject to any disclaimer, the term of this patent is extended or adjusted under 35 U.S.C. 154(b) by 0 days.

(21) Appl. No.: 10/514,500

(22) PCT Filed: May 15, 2003

(86) PCT No.: PCT/DK03/00318

§ 371 (c)(1),
(2), (4) Date: Nov. 15, 2004

(87) PCT Pub. No.: WO03/097601

PCT Pub. Date: Nov. 27, 2003

(65) Prior Publication Data

US 2005/0215588 A1    Sep. 29, 2005

Related U.S. Application Data

(60) Provisional application No. 60/380,836, filed on May 17, 2002.

(51) Int. Cl.
C07D 213/02    (2006.01)
A61K 31/4425    (2006.01)
(52) U.S. Cl. .................... 514/352; 546/306
(58) Field of Classification Search ............ 546/306; 514/352
See application file for complete search history.

(56) References Cited

U.S. PATENT DOCUMENTS

| | | |
|---|---|---|
| 5,919,816 A | 7/1999 | Hausheer et al. |
| 6,525,077 B2 | 2/2003 | Binderup et al. |
| 2003/0045515 A1 | 3/2003 | Binderup et al. |
| 2006/0014804 A1 | 1/2006 | Binderup |

FOREIGN PATENT DOCUMENTS

| | | |
|---|---|---|
| EP | 0 660 823 B1 | 8/1996 |
| WO | WO-98/54141 A1 | 12/1998 |
| WO | WO-98/54142 A1 | 12/1998 |
| WO | WO-98/54143 A1 | 12/1998 |
| WO | WO-98/54144 A | 12/1998 |
| WO | WO-98/54145 A1 | 12/1998 |
| WO | WO-00/61559 A | 10/2000 |
| WO | WO-00/61561 A1 | 10/2000 |
| WO | WO-02/42265 A | 5/2002 |
| WO | WO-02/094322 A2 | 11/2002 |
| WO | WO-03/97601 A1 | 11/2003 |
| WO | WO-03/097602 A1 | 11/2003 |

OTHER PUBLICATIONS

Davidsen et al., "N-(acyloxyalkyl) pyridinium salts as soluble prodrugs of a potent platelet activating factor antagonist", Journal of Medicinal Chemistry, Dec. 23, 1994, vol. 37, No. 26, pp. 4423-4429.
Bodor et al., "Soft alkylating compounds as potential antitumor agents", Journal of Medicinal Chemistry, 1980, vol. 23, No. 5, pp. 566-569.
Hjamaa, P. et al. "CHS 828, a Novel Pyridyl Cyanoguanidine with Potent Antitumor Activity in Vitro and in Vivo," Cancer Research 59, 5751-5757, Nov. 15,1999.
Schou, C. et al. "Novel Cyanoguanidines with Potent Oral Antitumour Activity," Bioorganic & Medicinal Chemistry Letters, vol. 7, No. 24, pp. 3095-3100, 1997.
Svensson, A. et al. "CHS 828 Inhibits Neuroblastoma Growth in Mice Alone and in Combination with Antiangiogenic Drugs,"Pediatric Research, vol. 51, No. 5, 2002, pp. 607-611.
Olsen, L.S. et al., "Anticancer Agent CHS 828 Suppresses Nuclear Facor$_K$B Activity in Cancer Cells through Downregulation of IKK Activity", Int. J. Cancer, vol. 111, pp. 198-205, 2004.

Primary Examiner—Zinna N. Davis
(74) Attorney, Agent, or Firm—Wilmer Cutler Pickering Hale and Dorr LLP

(57) ABSTRACT

Pyridyl cyanoguanidine compounds of the general formula I wherein A, $X_1$, $X_2$, $X_3$, $Y_1$, $Y_2$, $Y_3$, $R_1$, $R_2$, $R_5$, $R_6$ and n are as indicated in the description are suitable as prodrugs in human and veterinary therapy of proliferative diseases such as cancers.

18 Claims, No Drawings

CYANOGUANIDINE PRODRUGS

FIELD OF INVENTION

The present invention relates to novel pyridyl cyanoguanidine prodrugs and their inclusion in pharmaceutical compositions, as well as their use in the manufacture of medicaments.

BACKGROUND OF THE INVENTION

Pyridyl cyanoguanidines such as pinacidil (N-1,2,2-trimethylpropyl-N'-cyano-N"-(4-pyridyl)guanidine) were originally discovered to be potassium channel openers and were consequently developed as antihypertensive agents. Replacement of the side chain of pinacidil by longer aryl-containing side chains caused a loss of the antihypertensive activity, but such compounds were, on the other hand, found to show antitumour activity on oral administration in a rat model carrying Yoshida ascites tumours.

Different classes of pyridyl cyanoguanidines with antiproliferative activity are disclosed in, for instance, EP 660 823, WO 98/54141, WO 98/54143, WO 98/54144, WO 98/54145, WO 00/61559 and WO 00/61561. The structure-activity relationships (SAR) of such compounds are discussed in C. Schou et al., *Bioorganic and Medicinal Chemistry Letters* 7(24), 1997, pp. 3095–3100, in which the antiproliferative effect of a number of pyridyl cyanoguanidines was tested in vitro on different human lung and breast cancer cell lines as well as on normal human fibroblasts. The compounds were also tested in vivo in nude mice carrying a human lung cancer tumour xenograft. Based on the SAR analysis, a specific compound (N-(6-(4-chlorophenoxy)hexyl)-N'-cyano-N"-(4-pyridyl)guanidine) was selected for its high antiproliferative activity in vitro and potent antitumour activity in the nude mouse model.

P-J V Hjarnaa et al., *Cancer Res.* 59, 1999, pp. 5751–5757, report on the results of further testing of the compound N-(6-(4-chlorophenoxy)hexyl)-N'-cyano-N"-(4-pyridyl)guanidine in in vitro and in vivo tests. The compound exhibited a potency in vitro which was comparable to that of the reference cytostatic agents daunorubicin and paclitaxel, while showing considerably less antiproliferative activity on normal human endothelial cells. In in vivo tests using nude mice transplanted with human tumour cells, the compound showed substantial antitumour activity, also against tumour cells that were resistant to conventional anticancer drugs such as paclitaxel.

SUMMARY OF THE INVENTION

While, as indicated above, pyridyl cyanoguanidines are promising antitumour agents with an extremely interesting activity profile, they are highly lipophilic and consequently sparingly soluble compounds and are, as such, generally available for oral administration only. However, many cancer patients are in a severely debilitated condition as a result of their illness giving rise to problems with patient compliance with respect to oral administration of drugs.

It is therefore an object of the present invention to provide pyridyl cyanoguanidines in the form of prodrugs with an improved solubility profile which prodrugs may be included in pharmaceutical compositions suitable for parenteral administration, i.e. liquid compositions in which the prodrug is dissolved in sufficient amounts to be converted to therapeutically effective quantities of the active compound on administration of the composition. The compounds of the present invention exhibit good solubility in water, even at pH values around physiological pH making them ideal candidates for parenteral administration.

Furthermore, it has been found that pyridyl cyanoguanidine prodrugs of the invention exhibit an improved gastrointestinal absorption on oral administration. Consequently, it is another object of the invention to provide oral formulations of pyridyl cyanoguanidines as prodrugs with improved bioavailability.

Accordingly, the present invention relates to a compound of the general formula I

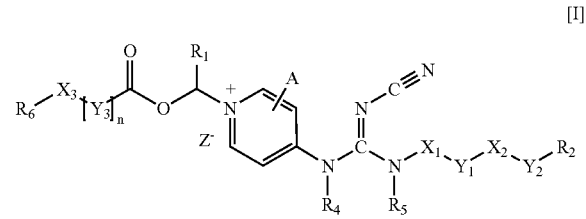

[I]

wherein $X_1$ is a straight, branched and/or cyclic hydrocarbon diradical, optionally substituted with one or more hydroxy, halogen, nitro, amino or cyano;

$X_2$ is a bond; a straight, branched and/or cyclic hydrocarbon diradical, optionally substituted with one or more hydroxy, halogen, nitro, amino, cyano, aminosulfonyl, alkylsulfonylamino, alkylcarbonyl, formyl, aminocarbonyl or alkylcarbonylamino; a heteroarylene or non-aromatic heterocyclic hydrocarbon diradical, all of which are optionally substituted with one or more straight, branched and/or cyclic non-aromatic hydrocarbon radical, hydroxyl, halogen, amino, nitro, cyano, aminosulfonyl, alkylsulfonylamino, alkylcarbonyl, formyl, aminocarbonyl or alkylcarbonylamino;

$X_3$ is a straight, branched and/or cyclic hydrocarbon diradical, optionally substituted with one or more substituents selected from the group consisting of hydroxy, halogen, nitro, amino, cyano, aminosulfonyl, alkylsulfonylamino, alkylcarbonyl, formyl, aminocarbonyl or alkylcarbonylamino; with the proviso that when $R_6$ is $—NH_2$, $X_3$ comprises five carbon atoms or more; and with the further proviso that when n is 0 and $R_6$ is a heterocyclic ring or ring system with 3–10 ring atoms, wherein at least 1 ring atom constitutes an aliphatic amine, $X_3$ may also be a bond;

$Y_1$ is a bond, O, S, S(O), S(O)$_2$, C(O), NH—C(O) or C(O)—NH;

$Y_2$ is a bond, an ether diradical (R'—O—R"), an amine diradical (R'—N—R"), O, S, S(O), S(O)$_2$, C(O), NH—C(O), C(O)—NH, SO$_2$—N(R') or N(R')—SO$_2$ wherein R' and R" are independently straight or branched hydrocarbon diradicals containing up to 4 carbon atoms;

$Y_3$ is O;

$R_1$ is hydrogen or straight, branched and/or cyclic alkyl, optionally substituted with phenyl; or an aromatic hydrocarbon radical;

$R_2$ is hydrogen, or aryl or heteroaryl, both of which are optionally substituted with one or more substituent selected from the group consisting of halogen, trifluoromethyl, hydroxy, $C_{1-4}$alkoxy, nitro, cyano, $C_{1-4}$hydroxyalkyl or $C_{1-4}$alkyl, optionally substituted with halogen, hydroxy, cyano or nitro; tetrahydropyranyloxy, di-($C_{1-4}$ alkoxy)phosphinoyloxy or $C_{1-4}$ alkoxycarbonylamino;

$R_4$ and $R_5$ are independently hydrogen; a straight, branched and/or cyclic hydrocarbon radical, optionally substituted with halogen, hydroxyl, halogen, amino, nitro or cyano;

$R_6$ is an amino group or a heterocyclic ring or condensed ring system with 3–10 ring atoms, wherein at least 1 ring atom constitutes an aliphatic amine;

A is hydrogen, an optionally substituted, straight, branched and/or cyclic hydrocarbon radical, hydroxy, halogen, nitro, cyano, heteroaryl, heteroaralkyl or thiol;

n is 0 or 1; and $Z^-$ is a pharmaceutically acceptable anion, such as chloride, bromide, iodide, sulfate, methanesulfonate, p-toluenesulfonate, nitrate or phosphate.

Furthermore, the invention relates to a compound of formula II, which is the free base form of the compounds of formula I, provided $R_4$ is hydrogen

[II]

wherein A, $R_1$, $R_2$, $R_5$, $R_6$, $X_1$, $X_2$, $X_3$, $Y_1$, $Y_2$, $Y_3$ and n are as indicated above.

It is understood that the compounds of the present invention include any tautomeric forms, optical isomers or diastereoisomers thereof, either in pure form or as mixtures thereof. It is further understood that the invention includes pharmaceutically acceptable salts of compounds of formula I or II.

On administration of a compound of formula I or formula II to a patient, the ester or carbonate group $R_6$—$X_3$—$(Y_3)_n$—C(O)O—$CHR_1$— is hydrolysed enzymatically to liberate the active compound of formula III

[III]

wherein A, $R_2$, $R_4$, $R_5$, $X_1$, $X_2$, $Y_1$, and $Y_2$ are as indicated above, together with the aldehyde $R_1$CHO.

DETAILED DESCRIPTION OF THE INVENTION

Definitions

In the present context, the term "prodrug" is intended to indicate a derivative of an active compound which does not, or does not necessarily, exhibit the physiological activity of the active compound, but which may be subjected to enzymatic cleavage such as hydrolysis in vivo so as to release the active compound on administration of the prodrug. In this particular instance, the prodrug comprises the active compound which in itself is highly lipophilic provided with a side chain with predominantly hydrophilic properties imparting improved solubility characteristics to the prodrug, thereby making it more suitable for parenteral administration in the form of a solution or for oral administration to obtain an improved bioavailability. More specifically, the hydrophilic side chain selected for the compounds of the present invention comprises an ester or carbonate group of formula $R_6$—$X_3$—$(Y_3)_n$—C(O)O—$CHR_1$— (wherein $R_6$, $R_1$, $X_3$, $Y_3$ and n are as indicated above).

The term "alkyl" is intended to indicate a univalent radical derived from straight, branched or cyclic alkane by removing a hydrogen atom from any carbon atom, preferably comprising from 1–8 carbon atoms. The term includes the subclasses primary, secondary and tertiary alkyl, such as methyl, ethyl, n-propyl, isopropyl, n-butyl, sec.-butyl, isobutyl, tert.-butyl, isopentyl, isohexyl, cyclohexyl, cyclopentyl and cyclopropyl.

The term "aryl" is intended to indicate radicals of carbocyclic aromatic rings, optionally fused bi-, tri- or tetracyclic rings wherein at least one ring is aromatic, e.g. phenyl, naphthyl, indanyl, indenyl, 1,4-dihydronaphtyl, flourenyl or tetralinyl.

The term "heteroaryl" is intended to indicate radicals of heterocyclic aromatic rings, in particular 5- or 6-membered rings with 1–3 heteroatoms selected from O, S and N, or optionally fused bicyclic rings, of which at least one is aromatic, with 1–4 heteroatoms, e.g. pyrrolyl, furanyl, thiophenyl, imidazolyl, oxazolyl, thiazolyl, pyrazolyl, pyridyl, pyrimidyl, purinyl, quinolinyl, chromenyl or carbazolyl.

The term "aralkyl" is intended to indicate an aromatic ring with an alkyl side chain as defined above, e.g. benzyl.

The term "halogen" is intended to indicate fluoro, chloro, bromo or iodo.

The term "aminosulfonyl" indicates a radical of the formula —$S(O)_2NR^a_2$, wherein each $R^a$ independently represents either hydrogen or alkyl as defined above.

The term "alkylsulfonylamino" indicates a radical of the formula —$NR^a_2$—$S(O)_2$—$R^b$, wherein each $R^a$ independently represents hydrogen or alkyl as defined above, and $R^b$ represents alkyl as defined above.

The term "alkylcarbonyl" indicates a radical of the formula —$C(O)R^b$, wherein $R^b$ is as just described.

The term "amino" indicates a radical of the formula —$N(R^a)_2$, wherein each $R^a$ independently represents hydrogen or alkyl as defined above.

The term "alkylcarbonylamino" indicates a radical of the formula —$NR^aC(O)R^b$, wherein $R^a$ and $R^b$ are as just described.

The term "alkoxy" indicates a radical of the formula $OR^b$, wherein $R^b$ is as just described.

The term "alkoxycarbonyl" is intended to indicate a radical of the formula —$C(O)$—$OR^b$, wherein $R^b$ is as indicated above.

The term "aminoacylamino" is intended to indicate a radical of the formula —NH—C(O)—$R^c$—$NH_2$, wherein $R^c$ is a diradical known from any natural amino acid, $H_2N$—$R^c$—COOH, or its enantiomer.

The term "aminocarbonyl" is intended to indicate a radical of the formula —C(O)—$NR^a_2$, wherein each $R^a$ independently represent hydrogen or alkyl as defined above.

The term "alkoxycarbonylamino" is intended to indicate a radical of the formula —$NR^a$—C(O)—$OR^b$, wherein $R^a$ and $R^b$ are as indicated above.

The term "hydrocarbon" is intended to indicate a compound comprising only hydrogen and carbon atoms, it may contain one or more double or triple carbon-carbon bonds, and it may comprise cyclic moieties in combination with branched or linear moieties. Said hydrocarbon preferably comprises 1–18, e.g. 1–12 carbon atoms. The term may be qualified as "non-aromatic heterocyclic", which is intended to indicate saturated or partly saturated cyclic compounds with 1–3 heteroatoms selected from O, S or N or optionally fused bicyclic rings with 1–4 heteroatoms, such as pyrrolidinyl, 3-pyrrolinyl, tetrahydrofuranyl, tetrahydrothiophenyl, piperidinyl, piperazinyl.

The term "a heterocyclic ring or condensed ring system with 3–10 ring atoms, wherein at least 1 ring atom constitutes an aliphatic amine" is intended to include radicals, such as pyrrolidinyl, piperidyl, hexahydro-1H-azapinyl, imidazolidinyl, piperazinyl, decahydro-isoquinolinyl, octahydro-isoindolyl, 1,2,3,4-tetrahydro-isoquinolinyl, 2,3-dihydro-1H-isoindolyl and morpholinyl The term "pharmaceutically acceptable salt" is intended to indicate salts prepared by reacting a compound of formula I or II comprising a basic group with a suitable inorganic or organic acid, e.g. hydrochloric, hydrobromic, hydroiodic, sulfuric, nitric, acetic, phosphoric, lactic, maleic, phthalic, citric, proplonic, benzoic, glutaric, gluconic, methanesulfonic, salicylic, succinic, tartaric, toluenesulfonic, sulfamic or fumaric acid.

Preferred Embodiments of the Compound of Formula I or II

In a preferred embodiment of the invention, $X_2$ and $Y_1$ are both bonds, while $X_1$ is a straight, branched or cyclic, saturated or unsaturated hydrocarbon diradical with 4 to 20 carbon atoms; $Y_2$ is O, S, C(O) or a bond;

$R_2$ is aryl or heteroaryl, both of which are optionally substituted by one or more substituent selected from the group consisting of halogen, trifluoromethyl, hydroxy, $C_{1-4}$alkoxy, nitro, cyano, $C_{1-4}$hydroxyalkyl or $C_{1-4}$alkyl, optionally substituted with halogen, hydroxy, cyano or nitro; tetrahydropyranyloxy, di-($C_{1-4}$ alkoxy)phosphinoyloxy or $C_{1-4}$ alkoxycarbonylamino;

$X_3$ is a straight hydrocarbon diradical comprising from 1 to 10 carbon atoms.

$R_6$ is —$NH_2$ or piperidyl, attached at the 2, 3 or 4 position to $X_3$, and in particular at the 3 or 4 position;

$R_1$ is hydrogen, straight or branched $C_{1-4}$alkyl, aralkyl or aryl;

A, $R_4$ and $R_5$ are all hydrogen;

n is 0 or 1;

and $Z^-$ is a pharmaceutically acceptable anion, such as chloride, bromide, iodide, sulfate, methanesulfonate, p-toluenesulfonate or nitrate.

In a preferred embodiment of the compounds of formula I or II, $R_2$ is aryl and in particular phenyl, optionally substituted by one or more substituent selected from the group consisting of halogen, trifluoromethyl, hydroxy, $C_{1-4}$alkoxy, nitro, cyano, $C_{1-4}$hydroxyalkyl or $C_{1-4}$alkyl, optionally substituted with halogen, hydroxy, cyano or nitro. A particular preferred substituent is halogen, such as chloro.

In a preferred embodiment of the compounds of formula I or II, $Y_1$ is a bond and $Y_2$ is O.

In a further preferred embodiment of the compounds of formula I or II, $X_1$ is a $C_{4-12}$ hydrocarbon diradical and $X_2$ is a bond.

Examples of Specific Compounds of Formula I are

1-[2-(4-Piperidyl)-ethoxy-carbonyloxymethyl]-4-[N'-cyano-N"-(6-(4-chloro-phenoxy)-1-hexyl)-N-guanidino]-pyridinium chloride, hydrochloride;

1-[3-Piperidyl-methoxy-carbonyloxymethyl]-4-[N'-cyano-N"-(6-(4-chloro-phenoxy)-1-hexyl)-N-guanidino]-pyridinium chloride, hydrochloride;

1-[4-Piperidyl-methoxy-carbonyloxymethyl]-4-[N'-cyano-N"-(6-(4-chloro-phenoxy)-1-hexyl)-N-guanidino]-pyridinium chloride, hydrochloride;

1-[8-Amino-1-octyloxy-carbonyloxymethyl]-4-[N'-cyano-N"-(6-(4-chlorophenoxy)-1-hexyl)-N-guanidino]-pyridinium chloride, hydrochloride;

1-[4-Piperidyl-carbonyloxymethyl]-4-[N'-cyano-N"-(6-(4-chloro-phenoxy)-1-hexyl)-N-guanidino]-pyridinium chloride, hydrochloride;

As described above, an advantage of the prodrug forms of cyanoguanidines of the present invention is an increased solubility compared to the solubility of the cyanoguanidines themselves. The cause for said increase lies with at least two factors, i.e. the positive charge at the pyridine nitrogen, and the hydrophilic character of the prodrog moiety, i.e.

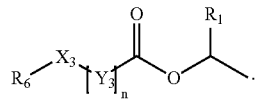

Pyridines in general have $pK_B$ values around 9. This indicates that if pH is raised from acid pH values, e.g. 3 to physiological pH then the compounds of the present invention will be transformed from compounds of formula I to the corresponding free base, i.e. to compounds of formula II. At physiological pH, the positive charge at the pyridine nitrogen has thus largely disappeared, and this will lower the solubility of the compounds. It is believed to be a particular advantage of the compounds of the present invention that the prodrug moiety at $R_6$ bears a unit charge, or at least a fraction of a unit charge, at physiological pH. As defined, $R_6$ comprises an aliphatic amine moiety, and it is well-known that aliphatic amines have $pK_B$ values in the 3–5 range [Frenna, *J. Chem. Soc. Perkin Trans. II,* 1865, 1985], which implies that the amine moiety is mainly protonated at physiological pH. The protonation gives rise to a charge which increases solubility.

Moreover, the following compounds is found to be particular useful in the preparation of compounds of formula I and II Chloromethyl 2-(1-(tert-butoxycarbonyl)-4-piperidyl)-ethyl carbonate;

Chloromethyl 1-(tert-butoxycarbonyl)-3-piperidyl-methyl carbonate;

Chloromethyl 1-(tert-butoxycarbonyl)-4-piperidyl-methyl carbonate;

Iodomethyl 2-(1-(tert-butoxycarbonyl)-4-piperidyl)-ethyl carbonate;

Iodomethyl 1-(tert-butoxycarbonyl)-3-piperidyl-methyl carbonate;

Iodomethyl 1-(tert-butoxycarbonyl)-4-piperidyl-methyl carbonate;

Chloromethyl 8-(tert-butoxycarbonylamino)-1-octyl carbonate;

Iodomethyl 8-(tert-butoxycarbonylamino)-1-octyl carbonate;

Chloromethyl N-tert-butoxycarbonyl-4-piperidylcarboxylate;

Iodomethyl N-tert-butoxycarbonyl-4-piperidylcarboxylate;

1-[2-[1-(tert-Butoxycarbonyl)-4-piperidyl]-ethoxy-carbonyloxymethyl]-4-[N'-cyano-N"-(6-(4-chlorophenoxy)-1-hexyl)-N-guanidino]-pyridinium iodide;

1-[1-(tert-Butoxycarbonyl)-3-piperidyl-methoxy-carbony-loxymethyl]-4-[N'-cyano-N''-(6-(4-chlorophenoxy)-1-hexyl)-N-guanidino]-pyridinium iodide;

1-[1-(tert-Butoxycarbonyl)-4-piperidyl-methoxy-carbony-loxymethyl]-4-[N'-cyano-N''-(6-(4-chlorophenoxy)-1-hexyl)-N-guanidino]-pyridinium iodide;

1-[8-(N-tert-Butoxycarbonylamino)-1-octyloxy-carbony-loxymethyl]-4-[N'-cyano-N''-(6-(4-chlorophenoxy)-1-hexyl)-N-guanidino]-pyridinium iodide; and 1-[1-(tert-Butoxycarbonyl)-4-piperidyl-carbonyloxym-ethyl]-4-[N'-cyano-N''-(6-(4-chlorophenoxy)-1-hexyl)-N-guanidino]-pyridinium iodide;

General Methods of Preparation

Compounds of formula I may be prepared by reacting a compound of formula III

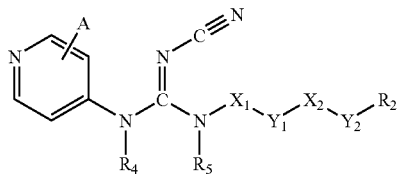

[III]

wherein A, $R_2$, $R_4$, $R_5$, $X_1$, $X_2$, $Y_1$ and $Y_2$ are as indicated in formula I, with a compound of formula IV

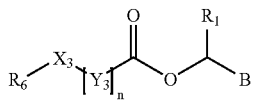

[IV]

wherein $R_1$, $R_6$, $X_3$, $Y_3$, and n are as indicated above, and B is a leaving group, such as Cl, Br or I. In addition $R_6$ and $X_3$ may optionally contain protecting groups.

The reaction of a compound of formula III with a compound of formula IV may be performed in a solvent-free environment or in an inert solvent such as acetonitrile at a temperature between room temperature and 150° C. to afford a compound of formula I optionally after removal of protecting groups.

The compounds of formula IV are known from the literature or may be prepared by methods well known to persons skilled in the art.

When n is 1, compounds of formula IV may be prepared by reacting a compound of formula V

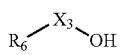

[V]

wherein $R_6$ and $X_3$ are as indicated in formula IV, with a compound of formula VI

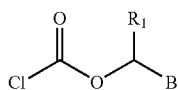

VI wherein $R_1$ and B are as indicated above.

The reaction between a compound of formula V and a compound of formula VI may be performed at a temperature between room temperature and −70° C. in an inert organic solvent, such as dichloromethane, in the presence of a suitable base such as pyridine.

When n is zero, compounds of formula IV in which B is chlorine may be prepared by reacting a compound of formula VII

[VII]

wherein $R_6$ and $X_3$ are as indicated in formula IV and $M^+$ is a suitable metal kation, e. g. an alkalimetal kation, or a tertiary ammonium ion, with a compound of formula VIII

X—CH(R$_1$)—Cl    VIII wherein $R_1$ is as indicated above and X is iodo, bromo or chlorosulfonyloxy.

The reaction between VII and VIII may be performed in a suitable solvent such as dimethylformamide at a suitable temperature, e.g. at room temperature, when X is iodo or bromo. When X is chlorosulfonyloxy the reaction may be performed under phase transfer conditions as described in *Synthetic Communications* 14, 857–864 (1984).

Compounds of formula IV in which B is chloro may be transformed into the corresponding compounds in which B is iodo by reaction with sodium iodide in acetone or acetonitrile.

The compounds of formulae V, VI, VII, VIII are either known from the literature or may be prepared by methods well known to persons skilled in the art.

Compounds of formula III are known from the literature and may be prepared by any one of the methods disclosed in, for instance, EP 660 823, WO 98/54141, WO 98/54143, WO 98/54144, WO 98/54145, WO 00/61559 and WO 00/61561.

A compound of formula I, provided that $R_4$ is hydrogen may be converted into the corresponding free base of formula II by treating a solution of a compound of formula I in an appropriate inert solvent, e.g. dichloromethane, with a suitable base, e.g. aqueous sodium bicarbonate. The free base of formula II may be reconverted into a salt of formula I by treating a solution of a compound of formula II in an appropriate inert solvent, e.g. dichloromethane, with a suitable acid of formula ZH, wherein Z is as indicated above.

Pharmaceutical Compositions

In another aspect, the invention relates to pharmaceutical formulations of a compound of formula I or II intended for the treatment of proliferative diseases. The formulations of the present invention, both for veterinary and for human medical use, comprise active ingredients in association with a pharmaceutically acceptable carrier(s) and optionally other therapeutic ingredient(s). The carrier(s) must be "acceptable" in the sense of being compatible with the other ingredients of the formulations and not deleterious to the recipient thereof.

Conveniently, the active ingredient comprises from 0.1–100% by weight of the formulation. Conveniently, a dosage unit of a formulation contain between 0.07 mg and 1 g of a compound of formula I or II.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations include e.g. those in a form suitable for oral (including sustained or timed release), rectal, parenteral (including subcutaneous, intraperitoneal, intramuscular, intraarticular and intravenous), transdermal, ophthalmic, topical, nasal or buccal administration.

The formulations may conveniently be presented in dosage unit form and may be prepared by any of the methods well known in the art of pharmacy, e.g as disclosed in Remington, *The Science and Practice of Pharmacy*, 20$^{th}$ ed., 2000. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units, such as capsules, sachets, tablets or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone. The active ingredients may also be administered in the form of a bolus, electuary or paste.

A tablet may be made by compressing or moulding the active ingredient optionally with one or more accessory ingredients. Compressed tablets may be prepared by compressing, in a suitable machine, the active ingredient(s) in a free-flowing form such as a powder or granules, optionally mixed by a binder, such as e.g. lactose, glucose, starch, gelatine, acacia gum, tragacanth gum, sodium alginate, carboxymethylcellulose, methylcellulose, hydroxypropylmethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent.

Formulations for rectal administration may be may in the form of suppositories in which the compound of the present invention is admixed with low melting water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. The formulation may be conveniently sterilised by for instance filtration through a bacteria retaining filter, addition of sterilising agent to the formulation, irradiation of the formulation or heating of the formulation. Liposomal formulations as disclosed in e.g. *Encyclopedia of Pharmaceutical Technology*, vol. 9, 1994, are also suitable for parenteral administration.

Alternatively, the compound of formula I may be presented as a sterile, solid preparation, e.g. a freeze-dried powder, which is readily dissolved in a sterile solvent immediately prior to use.

Transdermal formulations may be in the form of a plaster or a patch.

Formulations suitable ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in *Encyclopedia of Pharmaceutical Technology*, vol. 2, 1989, may also be used to present the active ingredient for ophthalmic administration.

Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops.

Formulations suitable for nasal or buccal administration include powder, self-propelling and spray formulations, such as aerosols and atomisers.

In addition to the aforementioned ingredients, the formulations of a compound of formula I or II may include one or more additional ingredients such as diluents, buffers, flavouring agents, colourant, surface active agents, thickeners, preservatives, e.g. methyl hydroxybenzoate (including antioxidants), emulsifying agents and the like.

In the systemic treatment using the present invention daily doses of from 0.001–500 mg per kilogram body weight, preferably from 0.002–100 mg/kg of mammal body weight, for example 0.003–20 mg/kg or 0.003 to 5 mg/kg of a compound of formula I or II is administered, typically corresponding to a daily dose for an adult human of from 0.01 to 37000 mg. However, the present invention also provides compounds and compositions intended for administration with longer intervals, e.g. every week, every three weeks or every month. In the topical treatment of dermatological disorders, ointments, creams or lotions containing from 0.1–750 mg/g, and preferably from 0.1–500 mg/g, for example 0.1–200 mg/g of a compound of formula I or II is administered. For topical use in ophthalmology ointments, drops or gels containing from 0.1–750 mg/g, and preferably from 0.1–500 mg/g, for example 0.1–200 mg/g of a compound of formula I or II is administered. The oral compositions are formulated, preferably as tablets, capsules, or drops, containing from 0.07–1000 mg, preferably from 0.1–500 mg, of a compound of formula I or II per dosage unit.

In a preferred embodiment, the invention provides pharmaceutical compositions comprising a compound of formula I or II in combination with one or more other pharmacologically active compounds used in the treatment of proliferative diseases. Examples of compounds used in the treatment of proliferative diseases which may be used together with compounds of the present invention include S-triazine derivatives such as altretamine; enzymes such as asparaginase; antibiotic agents such as bleomycin, dactinomycin, daunorubicin, doxorubicin, idarubicin, mitomycin, epirubicin and plicamycin; alkylating agents such as busulfan, carboplatin, carmustine, chlorambucil, cisplatin, cyclophosphamide, dacarbazine, ifosfamide, lomustine, mechlorethamine, melphalan, procarbazine and thiotepa;

antimetabolites such as cladribine, cytarabine, floxuridine, fludarabine, fluorouracil, hydroxyurea, mercaptopurine, methotrexate, gemcitabin, pentostatin and thioguanine; antimitotic agents such as etoposide, paclitaxel, teniposide, vinblastine, vinorelbin and vincristine; hormonal agents, e.g. aromatase inhibitors such as aminoglutethimide, corticosteroids, such as dexamethasone and prednisone, and luteinizing hormone releasing hormone (LH-RH); antiestrogens such as tamoxifen, formestan and letrozol; antiandrogens such as flutamide; biological response modifiers, e.g. lymphokines such as aldesleukin and other interleukines; interferon such as interferon-α; growth factors such as erythropoietin, filgrastim and sagramostim; differentiating agents such as vitamin D derivatives, e.g. seocalcitol, and all-trans retinoic acid; immunoregulators such as levamisole; and monoclonal antibodies, tumour necrosis factor α and angiogenesis inhibitors. Finally, ionising radiation, although not readily defined as a compound, is heavily depended on in the treatment of neoplastic diseases, and may be combined with the compounds of the present invention. Due to the severe side effects often experienced by patients receiving anti-neoplastic treatment it is often desirable also to administer therapeutics which are not in themselves anti-neoplastic, but rather help relieving the side effects of anti-neoplastic therapy. Such compounds include amifostin, leucovorin and mesna.

In particular, anti-neoplastic compounds, such as paclitaxel, fluorouracil, etoposide, cyclophospamide, cisplatin, carboplatin, vincristine, gemcitabine, vinorelbine, chlorambucil, doxorubicin and melphalan appear beneficial in the combination compositions of the present invention.

It is envisaged that the combination composition of the present invention may be provided as mixtures of the compounds or as individual compounds intended for simultaneous or sequential administration. It lies within the capabilities of a skilled physician or veterinarian to decide time intervals in a sequential administration regime.

In a further aspect, the invention relates to a method of treating or ameliorating proliferative diseases or conditions, the method comprising administering, to a patient in need thereof, a pharmaceutical composition comprising a compound of formula I or II, which compound is hydrolysed enzymatically upon administration to provide a compound of formula III, in an amount sufficient to effect treatment or amelioration of said proliferative disease or condition, optionally together with another anti-neoplastic compound and/or ionising radiation.

In particular, proliferative diseases or conditions to be treated by the present method include a variety of cancers and neoplastic diseases or conditions including leukaemia, acute myeloid leukaemia, chronic myeloid leukaemia, chronic lymphatic leukaemia, myelodysplasia, multiple myeloma, Hodgkin's disease or non-Hodgkin's lymphoma, small or non-small cell lung carcinoma, gastric, intestinal or colorectal cancer, prostate, ovarian or breast cancer, brain, head or neck cancer, cancer in the urinary tract, kidney or bladder cancer, malignant melanoma, liver cancer, uterine or pancreatic cancer.

Cyanoguanidines are also believed to be useful in the treatment of inflammatory diseases. In one aspect, the invention thus provides a method of treating inflammatory diseases, the method comprising administering to a patient an effective amount of a compound of the present invention, either alone or in combination with other therapeutically active compounds.

The invention also relates to the use of compounds of formula I or II, optionally together with other anti-neoplastic compounds, as indicated above, in the manufacture of medicaments. In particular, said medicament is intended to be used for the treatment of proliferative diseases, e.g. cancers as mentioned above.

As indicated above, it is preferred to administer the compounds of the invention parenterally, such as in a liquid, preferably aqueous, solution intended for intravenous injection or infusion. A suitable dosage of the compound of the invention will depend, inter alia, on the age and condition of the patient, the severity of the disease to be treated and other factors well known to the practising physician. The compound may be administered either orally or parenterally according to different dosing schedules, e.g. daily or with weekly intervals. In general a single dose will be in the range from 0.1 to 400 mg/kg bodyweight. Parenterally, the compound may be administered as a bolus (i.e. the entire dose is administered at once) or in divided doses two or more times a day or preferably as an intravenous infusion.

The invention is described in further detail in the following examples which are not in any way intended to limit the scope of the invention as claimed.

EXAMPLES

For $^1$H nuclear magnetic resonance (NMR) spectra (300 MHz) and $^{13}$C NMR (75.6 MHz) chemical shift values are quoted relative to internal tetramethylsilane (δ=0.00) or chloroform (δ=7.25) or deuteriochloroform (δ=76.81 for $^{13}$C NMR) standards. The value of a multiplet, either defined (singlet (s), doublet (d), triplet (t), quartet (q)) or not (broad (br)), at the approximate midpoint is given unless a range is quoted. The organic solvents used were anhydrous.

Preparation 1

Chloromethyl 2-(1-(tert-butoxycarbonyl)-4-piperidyl)-ethyl carbonate

Pyridine (3.22 ml) was added to an ice-cold solution of 2-(1-(tert-butoxycarbonyl)-4-piperidyl)-ethanol (7.6 g) in dichloromethane (33 ml) followed by chloromethyl chloroformate (3.23 ml) at such a rate that the temperature was kept below 10° C. After stirring overnight at room temperature the reaction mixture was washed twice with 0.5 M HCl followed by water and aqueous sodium bicarbonate. The organic phase was dried over magnesium sulfate, filtered and evaporated in vacuo to yield the title compound as a colourless oil.

$^1$H NMR (CDCl$_3$) δ=5.73 (s, 2H), 4.28 (t, 2H), 4.09 (d, 2H), 2.69 (t, 2H), 1.75–1.50 (m, 5H), 1.45 (s, 9H), 1.15 (m, 2H)

Preparation 2

Chloromethyl 1-(tert-butoxycarbonyl)-3-piperidyl-methyl carbonate

Prepared as described in Preparation 1 but substituting 1-(tert-butoxycarbonyl)-3-piperidyl-methanol for 2-(1-(tert-butoxycarbonyl)-4-piperidyl)-ethanol. Light yellow oil.

$^1$H NMR (CDCl$_3$) δ=5.73 (s, 2H), 4.11 (m, 2H), 4.0–3.75 (m, 2H), 3.00–2.60 (m, 2H), 2.00–1.60 (m, 3H), 1.45 (s, 9H), 1.29 (m, 2H)

Preparation 3

Chloromethyl 1-(tert-butoxycarbonyl)-4-piperidyl-methyl carbonate

Prepared as described in Preparation 1 but substituting 1-(tert-butoxycarbonyl)-4-piperidyl-methanol for 2-(1-(tert-butoxycarbonyl)-4-piperidyl)-ethanol. Light yellow oil.

¹H NMR (CDCl₃) δ=5.73 (s, 2H), 4.13 (d, 2H), 4.09 (d, 2H), 2.71 (d, 2H), 1.88 (m, 1H), 1.71 (d, 2H), 1.45 (s, 9H), 1.21 (m, 2H)

Preparation 4

Iodomethyl 2-(1-(tert-butoxycarbonyl)-4-piperidyl)-ethyl carbonate

Chloromethyl 2-(1-(tert-butoxycarbonyl)-4-piperidyl)-ethyl carbonate (4.9 g) was added to a solution of sodium iodide (9 g) in acetone (20 ml). After stirring at 40° C. for 2.5 hours the reaction mixture was cooled to room temperature, filtered and evaporated in vacuo. The residue was taken up in dichloromethane, washed with aqueous sodium bicarbonate and sodium thiosulfate, dried over magnesium sulfate, filtered and evaporated in vacuo. Purification on silica gel with hexane/ethyl acetate (2:1) as eluent gave the title compound as a light yellow oil.

¹H NMR (CDCl₃) δ=5.95 (s, 2H), 4.28 (t, 2H), 4.09 (d, 2H), 2.69 (t, 2H), 1.75–1.50 (m, 5H), 1.45 (s, 9H), 1.13 (m, 2H)

Preparation 5

Iodomethyl 1-(tert-butoxycarbonyl)-3-piperidyl-methyl carbonate

Prepared as described in Preparation 4 but substituting chloromethyl 1-(tert-butoxycarbonyl)-3-piperidyl-methyl carbonate for chloromethyl 2-(1-(tert-butoxycarbonyl)-4-piperidyl)-ethyl carbonate. Light yellow oil.

¹H NMR (CDCl₃) δ=5.95 (s, 2H), 4.11 (m, 2H), 4.0–3.75 (m, 2H), 3.00–2.60 (m, 2H), 2.00–1.60 (m, 3H), 1.45 (s, 9H), 1.29 (m, 2H)

Preparation 6

Iodomethyl 1-(tert-butoxycarbonyl)-4-piperidyl-methyl carbonate

Prepared as described in Preparation 4 but substituting chloromethyl 1-(tert-butoxycarbonyl)-4-piperidyl-methyl carbonate for chloromethyl 2-(1-(tert-butoxycarbonyl)-4-piperidyl)-ethyl carbonate. Light yellow oil.

¹H NMR (CDCl₃) δ=5.95 (s, 2H), 4.13 (m, 2H), 4.08 (d, 2H), 2.70 (t, 2H), 187 (m, 1H), 1.70 (d, 2H), 1.46 (s, 9H), 1.20 (m, 2H)

Preparation 7

Chloromethyl 8-(tert-butoxycarbonylamino)-1-octyl carbonate

A solution of pyridine (1.57 ml) and 8-(tert-butoxycarbonylamino)-1-octanol (4 g) in dichloromethane (40 ml) was cooled in dry-ice. Precipitation occurred during cooling and chloromethyl chloroformate (1.6 ml) was added to the stirred suspension at such a rate that the temperature was kept below −50° C. After stirring for 2 hours below −50° C. the cooling bath was removed and the temperature was allowed to rise to room temperature. The mixture was washed twice with 0.5 M HCl followed by water, aqueous sodium bicarbonate and saturated sodium chloride. The organic phase was dried over magnesium sulfate, filtered and evaporated in vacuo to yield the title compound as a colourless oil.

¹H NMR (CDCl₃) δ=5.73 (s, 2H), 4.52 (br, 1H), 4.22 (t, 2H), 3.10 (q, 2H), 1.69 (m, 2H), 1.44 (s, 9H), 1.55–1.20 (m, 10H)

Preparation 8

Iodomethyl 8-(tert-butoxycarbonylamino)-1-octyl carbonate

This compound was prepared as described in Preparation 4 but substituting chloromethyl 8-(tert-butoxycarbonylamino)-1-octyl carbonate for chloromethyl 2-(1-(tert-butoxycarbonyl)-4-piperidyl)-ethyl carbonate. Light yellow oil.

¹H NMR (CDCl₃) δ=5.95 (s, 2H), 4.51 (br, 1H), 4.21 (t, 2H), 3.10 (q, 2H), 1.68 (m, 2H), 1.44 (s, 9H), 1.55–1.20 (m, 10H)

Preparation 9

Chloromethyl N-tert-butoxycarbonyl-4-piperidylcarboxylate

To a solution of N-tert-butoxycarbonyl-4-piperidyl-carboxylic acid (6.4 g) in dichloromethane (30 ml) was added water (30 ml), sodium bicarbonate (8.91 g) and tetrabutylammonium hydrogensulfate (0.95 g). The mixture was stirred at room temperature while chloromethyl chlorosulfate (3.19 ml) was added slowly. After stirring for a further 30 minutes the organic phase was separated and evaporated in vacuo. The crude product was distributed between diethyl ether and water. The organic phase was separated, dried and evaporated to yield the title compound as an oil.

¹³C NMR (CDCl₃) δ=172.6, 154.6, 79.7, 68.7, 42.8, 40.8, 28.4, 27.5

Preparation 10

Iodomethyl N-tert-butoxycarbonyl-4-piperidylcarboxylate

Prepared as described in Preparation 4 but substituting chloromethyl N-tert-butoxycarbonyl-4-piperidylcarboxylate for chloromethyl 2-(1-(tert-butoxycarbonyl)-4-piperidyl)-ethyl carbonate. Light yellow oil.

¹³C NMR (CDCl₃) δ=172.6, 154.6, 79.7, 42.8, 41.0, 30.5, 28.4, 27.4

Preparation 11

1-[2-[1-(tert-Butoxycarbonyl)-4-piperidyl]-ethoxy-carbonyloxymethyl]-4-[N'-cyano-N''-(6-(4-chlorophenoxy)-1-hexyl)-N-guanidino]-pyridinium iodide.

Iodomethyl 2-[1-(tert-butoxycarbonyl)-4-piperidyl]-ethyl carbonate (5 g) was added to a hot solution of N-(6-(4-chlorophenoxy)-1-hexyl)-N'-cyano-N''-(4-pyridyl)-guanidine (2.8 g) in dry acetonitrile (110 ml) followed by reflux for 20 minutes. After cooling to room temperature and concentration in vacuo, the title compound crystallised and was isolated by filtration. Recrystallisation from acetonitrile gave the title compound as light yellow crystals.

¹H NMR (CDCl₃) δ=11.24 (br, 1H), 8.58 (d, 2H), 8.24 (br, 2H), 7.81 (br, 1H), 7.20 (d, 2H), 6.82 (d, 2H), 6.19 (s, 2H), 4.26 (t, 2H), 4.08 (d, 2H), 3.94 (t, 2H), 3.77 (q, 2H), 2.67 (t, 2H), 1.78 (m, 4H), 1.64 (m, 4H), 1.52 (m, 5H), 1.44 (s, 9H), 1.14 (m, 2H)

Preparation 12

1-[1-(tert-Butoxycarbonyl)-3-piperidyl-methoxy-carbonyloxymethyl]-4-[N'-cyano-N''-(6-(4-chlorophenoxy)-1-hexyl)-N-guanidino]-pyridinium iodide.

Iodomethyl 1-(tert-butoxycarbonyl)-3-piperidyl-methyl carbonate (5.4 g) was added to a hot solution of N-(6-(4-chlorophenoxy)-1-hexyl)-N'-cyano-N''-(4-pyridyl)-guanidine (2.8 g) in dry acetonitrile (110 ml) followed by reflux for 20 minutes. After cooling to room temperature and concentration in vacuo, ethyl acetate was added and the title compound crystallised and was isolated by filtration. Recrystallisation from ethyl acetate gave the title compound as light yellow crystals.

¹H NMR (CDCl₃) δ=11.28 (br, 1H), 8.57 (d, 2H), 8.27 (br, 2H), 7.85 (br, 1H), 7.20 (d, 2H), 6.82 (d, 2H), 6.19 (s, 2H), 4.10 (d, 2H), 3.94 (t, 2H), 3.87 (m, 2H), 3.79 (m, 2H), 2.93 (m, 1H), 2.71 (m, 1H), 2.00–1.48 (m, 11H), 1.44 (s, 9H), 1.26 (m, 2H)

Preparation 13

1-[1-(tert-Butoxycarbonyl)-4-piperidyl-methoxy-carbonyloxymethyl]-4-[N'-cyano-N''-(6-(4-chlorophenoxy)-1-hexyl)-N-guanidino]-pyridinium iodide.

Iodomethyl 1-(tert-butoxycarbonyl)-4-piperidyl-methyl carbonate (9 g) was added to a hot solution of N-(6-(4-chlorophenoxy)-1-hexyl)-N'-cyano-N''-(4-pyridyl)-guanidine (4 g) in dry acetonitrile (160 ml) followed by reflux for 20 minutes. After cooling to room temperature and concentration in vacuo, ethyl acetate was added and the title compound crystallised and was isolated by filtration as a light yellow powder.

$^1$H NMR (CDCl$_3$) δ=11.25 (br, 1H), 8.57 (d, 2H), 8.25 (br, 2H), 7.96 (br, 1H), 7.19 (d, 2H), 6.83 (d, 2H), 6.19 (s, 2H), 4.12 (br, 2H), 4.06 (d, 2H), 3.93 (t, 2H), 3.77 (t, 2H), 2.69 (t, 2H), 1.93–1.48 (m, 11H), 1.45 (s, 9H), 1.18 (m, 2H)

Preparation 14

1-[8-(N-tert-Butoxycarbonylamino)-1-octyloxy-carbonyloxymethyl]-4-[N'-cyano-N''-(6-(4-chlorophenoxy)-1-hexyl)-N-guanidino]-pyridinium iodide.

Iodomethyl 8-(tert-butoxycarbonylamino)-1-octyl carbonate (5.47 g) was added to a hot solution of N-(6-(4-chlorophenoxy)-1-hexyl)-N'-cyano-N''-(4-pyridyl)-guanidine (3.16 g) in dry acetonitrile (140 ml) followed by reflux for 20 minutes. After cooling to room temperature the title compound crystallised and after further cooling in ice the crystalline product was isolated by filtration.

$^{13}$C NMR (CDCl$_3$) δ=157.7, 156.0, 154.9, 153.8, 143.8, 129.2, 125.2, 115.8, 114.4, 80.4, 79.1, 70.5, 68.0, 43.0, 40.5, 30.0, 29.2, 29.0, 28.9, 28.4, 28.2, 26.6, 26.3, 25.4, 25.4

Preparation 15

1-[1-(tert-Butoxycarbonyl)-4-piperidyl-carbonyloxymethyl]-4-[N'-cyano-N''-(6-(4-chlorophenoxy)-1-hexyl)-N-guanidino]-pyridinium iodide.

Iodomethyl N-tert-butoxycarbonyl-4-piperidylcarboxylate (6.52 g) was added to a hot solution of N-(6-(4-chlorophenoxy)-1-hexyl)-N'-cyano-N''-(4-pyridyl)-guanidine (4.38 g) in dry acetonitrile (170 ml) followed by reflux for 20 minutes. After cooling to room temperature and concentration in vacuo the title compound crystallised and after further cooling in ice the crystalline product was isolated by filtration.

$^{13}$C NMR (CDCl$_3$) δ=173.5, 157.7, 154.6, 154.5, 153.9, 143.9, 129.3, 125.2, 115.9, 114.5, 80.0, 77.7, 68.0, 43.0, 40.6, 29.2, 28.9, 28.4, 27.6, 26.3, 25.5

Example 1

1-[2-(4-Piperidyl)-ethoxy-carbonyloxymethyl]-4-[N'-cyano-N''-(6-(4-chloro-phenoxy)-1-hexyl)-N-guanidino]-pyridinium chloride, hydrochloride.

A solution of 1-[2-[1-(tert-butoxycarbonyl)-4-piperidyl]-ethoxy-carbonyloxy-methyl]-4-[N'-cyano-N''-(6-(4-chlorophenoxy)-1-hexyl)-N-guanidino]-pyridinium iodide (1.9 g) in dichloromethane (60 ml) was shaken with an excess of aqueous sodium bicarbonate and sodium thiosulfate. The organic phase was dried over magnesium sulfate and filtered. After concentration in vacuo to about 15 ml the clear filtrate was cooled in ice with stirring and treated with an excess of hydrogen chloride in ether. The ice bath was removed and after stirring for 4 hours, the solvent was removed in vacuo. The residue crystallised upon addition of ethanol and after recrystallisation from methanol/ether the title compound was obtained in the form of nice colourless crystals.

$^1$H NMR (DMSO) δ=12.10 (br, 1H), 9.18 (br, 2H), 8.94 (br, 1H), 8.75 (d, 2H), 7.58 (br, 2H), 7.31 (d, 2H), 6.95 (d, 2H), 6.22 (s, 2H), 4.20 (t, 2H), 3.96 (t, 2H), 3.41 (m, 2H), 3.19 (m, 2H), 2.78 (q, 2H), 1.86–1.25 (m, 15H)

Example 2

1-[3-Piperidyl-methoxy-carbonyloxymethyl]-4-[N'-cyano-N''-(6-(4-chloro-phenoxy)-1-hexyl)-N-guanidino]-pyridinium chloride, hydrochloride.

A solution of 1-[1-(tert-butoxycarbonyl)-3-piperidyl-methoxy-carbonyloxy-methyl]-4-[N'-cyano-N''-(6-(4-chlorophenoxy)-1-hexyl)-N-guanidino]-pyridinium iodide (1.7 g) in dichloromethane (60 ml) was shaken with an excess of aqueous sodium bicarbonate and sodium thiosulfate. The organic phase was dried over magnesium sulfate and filtered. After concentration in vacuo to about 15 ml the clear filtrate was cooled in ice with stirring and treated with an excess of hydrogen chloride in ether. The ice bath was removed and after stirring for 4 hours, the solvent was removed in vacuo. The residue crystallised upon addition of ethanol and after filtration and recrystallisation from methanol/ether the title compound was obtained as colourless crystals.

$^1$H NMR (DMSO) δ=12.10 (br, 1H), 9.27 (br, 3H), 8.76 (d, 2H), 7.61 (br, 2H), 7.31 (d, 2H), 6.95 (d, 2H), 6.24 (s, 2H), 4.09 (m, 2H), 3.96 (t, 2H), 3.41 (br, 2H), 3.18 (d, 2H), 2.65 (m, 2H), 2.18 (br, 1H), 1.85–1.13 (m, 12H)

Example 3

1-[4-Piperidyl-methoxy-carbonyloxymethyl]-4-[N'-cyano-N''-(6-(4-chloro-phenoxy)-1-hexyl)-N-guanidino]-pyridinium chloride, hydrochloride.

A solution of 1-[1-(tert-butoxycarbonyl)-4-piperidyl-methoxy-carbonyloxy-methyl]-4-[N'-cyano-N''-(6-(4-chlorophenoxy)-1-hexyl)-N-guanidino]-pyridinium iodide (1 g) in dichloromethane (30 ml) was shaken with an excess of aqueous sodium bicarbonate and sodium thiosulfate. The organic phase was dried over magnesium sulfate and filtered. After concentration in vacuo to about 15 ml the clear filtrate was cooled in ice with stirring and treated with an excess of hydrogen chloride in ether. The ice bath was removed and after stirring for 4 hours, the solvent was removed in vacuo to yield the title compound as a colourless foam.

$^1$H NMR (DMSO) δ=12.05 (br, 1H), 9.19 (br, 2H), 8.93 (br, 1H), 8.78 (d, 2H), 7.65 (br, 2H), 7.31 (d, 2H), 6.95 (d, 2H), 6.24 (s, 2H), 4.50 (d, 2H), 3.96 (t, 2H), 3.42 (q, 2H), 3.22 (d, 2H), 2.82 (m, 2H), 1.8–1.25 (m, 13H)

Example 4

1-[8-Amino-1-octyloxy-carbonyloxymethyl]-4-[N'-cyano-N''-(6-(4-chlorophenoxy)-1-hexyl)-N-guanidino]-pyridinium chloride, hydrochloride Prepared as described in Example 1 but substituting 1-[8-(N-tert-butoxycarbonylamino)-1-octyloxy-carbonyloxymethyl]-4-[N'-cyano-N''-(6-(4-chlorophenoxy)-1-hexyl)-N-guanidino]-pyridinium iodide for 1-[2-[1-(tert-butoxycarbonyl)-4-piperidyl]-ethoxy-carbonyloxy-methyl]-4-[N'-cyano-N''-(6-(4-chlorophenoxy)-1-hexyl)-N-guanidino]-pyridinium iodide. Light yellow crystals.

$^{13}$C NMR (DMSO) δ=157.4, 154.9, 153.0, 144.9, 129.1, 123.9, 116.1, 115.0, 112.7, 80.1, 68.9, 67.6, 42.1, 28.3, 28.2, 27.7, 26.7, 25.7, 25.6, 25.0, 24.8

Example 5

1-[4-Piperidyl-carbonyloxymethyl]-4-[N'-cyano-N''-(6-(4-chloro-phenoxy)-1-hexyl)-N-guanidino]-pyridinium chloride, hydrochloride.

Prepared as described in Example 2 but substituting 1-[1-(tert-butoxycarbonyl)-4-piperidyl-carbonyloxymethyl]-4-[N'-cyano-N''-(6-(4-chlorophenoxy)-1-hexyl)-N-guanidino]-pyridinium iodide for 1-[2-[1-(tert-butoxycarbonyl)-4-piperidyl]-ethoxy-carbonyloxy-methyl]-4-[N'-cyano-N''-(6-(4-chlorophenoxy)-1-hexyl)-N-guanidino]-pyridinium iodide. Crystalline powder.

$^{13}$C NMR (DMSO) δ=172.2, 157.4, 154.8, 144.8, 129.1, 123.9, 116.1, 115.0, 78.1, 67.6, 41.7, 37.2, 28.3, 25.7, 25.0, 23.9

The invention claimed is:

1. A compound according to formula I

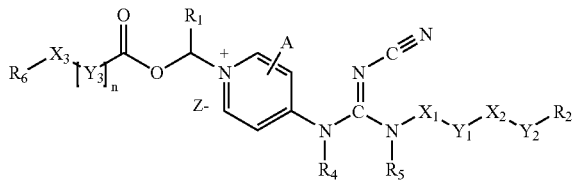

[I]

wherein $X_1$ is a straight, branched and/or cyclic hydrocarbon diradical, optionally substituted with one or more hydroxy, halogen, nitro, amino or cyano;

$X_2$ is a bond; a straight, branched and/or cyclic hydrocarbon diradical, optionally substituted with one or more hydroxy, halogen, nitro, amino, cyano, aminosulfonyl, alkylsulfonylamino, alkylcarbonyl, formyl, aminocarbonyl or alkylcarbonylamino; a heteroarylene or non-aromatic heterocyclic hydrocarbon diradical, all of which are optionally substituted with one or more straight, branched and/or cyclic non-aromatic hydrocarbon radical, hydroxyl, halogen, amino, nitro, cyano, aminosulfonyl, alkylsulfonylamino, alkylcarbonyl, formyl, aminocarbonyl or alkylcarbonylamino;

$X_3$ is a straight, branched and/or cyclic hydrocarbon diradical, optionally substituted with one or more substituents selected from the group consisting of hydroxy, halogen, nitro, amino, cyano, aminosulfonyl, alkylsulfonylamino, alkylcarbonyl, formyl, aminocarbonyl or alkylcarbonylamino; with the proviso that when $R_6$ is —NH$_2$, $X_3$ comprises five carbon atoms or more; and with the further proviso that when n is 0 and $R_6$ is a heterocyclic ring or ring system with 3–10 ring atoms, wherein at least 1 ring atom constitutes an aliphatic amine, $X_3$ may also be a bond;

$Y_1$ is a bond, O, S, S(O), S(O)$_2$, C(O), NH—C(O) or C(O)—NH;

$Y_2$ is a bond, an ether diradical (R'—O—R''), an amine diradical (R'—N—R''), O, S, S(O), S(O)$_2$, C(O), NH—C(O), C(O)—NH, SO$_2$—N(R') or N(R')—SO$_2$ wherein R' and R'' are independently straight or branched hydrocarbon diradicals containing up to 4 carbon atoms;

$Y_3$ is O;

$R_1$ is hydrogen or straight, branched and/or cyclic alkyl, optionally substituted with phenyl; or an aromatic hydrocarbon radical;

$R_2$ is hydrogen, or aryl or heteroaryl, both of which are optionally substituted with one or more substituent selected from the group consisting of halogen, trifluoromethyl, hydroxy, $C_{1-4}$alkoxy, nitro, cyano, $C_{1-4}$hydroxyalkyl or $C_{1-4}$alkyl, optionally substituted with halogen, hydroxyl, cyano or nitro; tetrahydropyranyloxy, di-($C_{1-4}$ alkoxy)phosphinoyloxy or $C_{1-4}$ alkoxycarbonylamino;

$R_4$ and $R_5$ are independently hydrogen; a straight, branched and/or cyclic hydrocarbon radical, optionally substituted with halogen, hydroxyl, halogen, amino, nitro or cyano;

$R_6$ is an amino group or a heterocyclic ring or condensed ring system with 3–10 ring atoms, wherein at least 1 ring atom constitutes an aliphatic amine;

A is hydrogen, an optionally substituted, straight, branched and/or cyclic hydrocarbon radical, hydroxy, halogen, nitro, cyano, heteroaryl, heteroaralkyl or thiol;

n is 0 or 1; and $Z^-$ is a pharmaceutically acceptable anion.

2. A compound of formula II

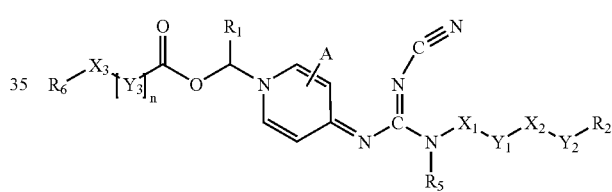

[II]

wherein A, $X_1$, $X_2$, $X_3$, $Y_1$, $Y_2$, $Y_3$, $R_1$, $R_2$, $R_5$, $R_6$ and n are as indicated in claim 1.

3. A compound according to claim 1 or 2 wherein $X_2$ and $Y_1$ are both bonds;

$X_1$ is a straight, branched or cyclic, saturated or unsaturated hydrocarbon diradical with 4 to 20 carbon atoms;

$Y_2$ is O, S, C(O) or a bond;

$R_2$ is aryl or heteroaryl, both of which are optionally substituted by one or more substituent selected from the group consisting of halogen, trifluoromethyl, hydroxy, $C_{1-4}$alkoxy, nitro, cyano, $C_{1-4}$hydroxyalkyl or $C_{1-4}$alkyl, optionally substituted with halogen, hydroxy, cyano or nitro; tetrahydropyranyloxy, di-($C_{1-4}$ alkoxy) phosphinoyloxy or $C_{1-4}$ alkoxycarbonylamino;

$X_3$ is a straight hydrocarbon diradical comprising from 1 to 10 carbon atoms;

$R_6$ is —NH$_2$ or piperidyl, attached at the 3 or 4 position to $X_3$;

$R_1$ is hydrogen, straight or branched $C_{1-4}$alkyl, aralkyl or aryl;

A, $R_4$ and $R_5$ are all hydrogen;

n is 0 or 1;

and $Z^-$ is chloride, bromide, iodide, sulfate, methanesulfonate, p-toluenesulfonate or nitrate.

4. A compound according to claim 1, wherein $R_2$ is aryl optionally substituted by one or more substituent selected from the group consisting of halogen, trifluoromethyl, hydroxy, $C_{1-4}$alkoxy, nitro, cyano, $C_{1-4}$hydroxyalkyl or $C_{1-4}$alkyl, optionally substituted with halogen, hydroxy, cyano or nitro.

5. A compound according to claim 1, wherein $R_2$ is phenyl or phenyl substituted by one or more substituent selected from the group consisting of halogen, trifluoromethyl, hydroxy, $C_{1-4}$alkoxy, nitro, cyano, $C_{1-4}$hydroxyalkyl or $C_{1-4}$alkyl, optionally substituted with halogen, hydroxyl, cyano or nitro.

6. A compound according to claim 5, wherein said substituent is chloro.

7. A compound according to claim 1, wherein $Y_1$ is a bond, and $Y_2$ is O.

8. A compound according to claim 1, wherein $X_1$ is a $C_{4-12}$ hydrocarbon diradical, and $X_2$ is a bond.

9. A compound according to claim 1 which is selected from the group consisting of
   1-[2-(4-Piperidyl)-ethoxy-carbonyloxymethyl]-4-[N'-cyano-N''-(6-(4-chloro-phenoxy)-1-hexyl)-N-guanidino]-pyridinium chloride, hydrochloride;
   1-[3-Piperidyl-methoxy-carbonyloxymethyl]-4-[N'-cyano-N''-(6-(4-chloro-phenoxy)-1-hexyl)-N-guanidino]-pyridinium chloride, hydrochloride;
   1-[4-Piperidyl-methoxy-carbonyloxymethyl]-4-[N'-cyano-N''-(6-(4-chloro-phenoxy)-1-hexyl)-N-guanidino]-pyridinium chloride, hydrochloride;
   1-[8-Amino-1-octyloxy-carbonyloxymethyl]-4-[N'-cyano-N''-(6-(4-chlorophenoxy)-1-hexyl)-N-guanidino]-pyridinium chloride, hydrochloride;
   1-[4-Piperidyl-carbonyloxymethyl]-4-[N'-cyano-N''-(6-(4-chloro-phenoxy)-1-hexyl)-N-guanidino]-pyridinium chloride, hydrochloride.

10. A compound according to claim 1, wherein $Z^-$ is an anion selected from the group consisting of chloride, bromide, iodide, sulfate, methanesulfonate, p-toluenesulfonate, nitrate and phosphate.

11. A pharmaceutical composition comprising a compound of formula I or II according to claim 1 or 2 together with a pharmaceutically acceptable excipient or diluent.

12. A composition according to claim 11, wherein the compound is dissolved in an appropriate, pharmaceutically acceptable solvent.

13. A composition according to claim 12 for parenteral administration, intravenous injection or infusion.

14. A composition according claim 11 further comprising one or more other anti-neoplastic compounds.

15. A composition according to claim 14, wherein said other antineoplastic compound(s) is selected from the group consisting of S-triazin derivatives, antibiotic agents, alkylating agents, anti-metabolites, anti-mitotic agents, hormonal agents, differentiating agents, biological response modifiers and angiogenesis inhibitors.

16. A composition according to claim 15, wherein the compound of formula I or II 1-[2-(4-Piperidyl)-ethoxy-carbonyloxymethyl]-4-[N'-cyano-N''-(6-(4-chloro-phenoxy)-1-hexyl)-N-guanidino]-pyridinium chloride, hydrochloride, and wherein the other anti-neoplastic agent(s) is selected from the group consisting of paclitaxel, fluorouacil, etoposide, cyclophosphamide, cisplatin, carboplatin, vincristine, gemcitabine, vinorelbine, chlorambucil, doxorubicin, melphalan and seocalcitol.

17. A pharmaceutical composition comprising, in separate containers and intended for sequential or simultaneous administration, a compound of formula I or II according to claim 1 or 2 and one or more other anti-neoplastic compound(s), together with pharmaceutically acceptable exipients or diluents.

18. A composition according to claim 12, wherein the pharmaceutically acceptable solvent is selected from the group consisting of water, isotonic saline, isotonic glucose solution, or a buffer solution.

* * * * *